United States Patent
Otani et al.

(10) Patent No.: US 9,694,209 B2
(45) Date of Patent: Jul. 4, 2017

(54) PARTICLE BEAM THERAPY SYSTEM (71) Applicant: MITSUBISHI ELECTRIC CORPORATION, Chiyoda-ku, Tokyo (JP)

(72) Inventors: Toshihiro Otani, Tokyo (JP); Syuhei Odawara, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/890,542

(22) PCT Filed: Aug. 29, 2013

(86) PCT No.: PCT/JP2013/073093
§ 371 (c)(1),
(2) Date: Nov. 11, 2015

(87) PCT Pub. No.: WO2015/029178
PCT Pub. Date: Mar. 5, 2015

(65) Prior Publication Data
US 2016/0101298 A1    Apr. 14, 2016

(51) Int. Cl.
*A61N 5/10* (2006.01)
*H05H 7/04* (2006.01)

(52) U.S. Cl.
CPC ......... *A61N 5/1079* (2013.01); *A61N 5/1077* (2013.01); *H05H 7/04* (2013.01);
(Continued)

(58) Field of Classification Search
None
See application file for complete search history.

(56) References Cited

U.S. PATENT DOCUMENTS 5,161,546 A    11/1992   Bronn
6,683,318 B1   1/2004    Haberer et al.
(Continued)

FOREIGN PATENT DOCUMENTS

JP   2009-502221 A   1/2009
JP   2009-217938 A   9/2009
(Continued)

OTHER PUBLICATIONS

International Search Report (PCT/ISA/210) mailed on Oct. 29, 2013, by the Japanese Patent Office as the International Searching Authority for International Application No. PCT/JP2013/073093.
(Continued)

*Primary Examiner* — Jack Berman
(74) *Attorney, Agent, or Firm* — Buchanan Ingersoll & Rooney PC (57) ABSTRACT

A particle beam transport section comprises a horizontal deflection electromagnet which deflects a particle beam to a direction which is parallel to an accelerator median plane of a circular accelerator, a first perpendicular electromagnet which deflects a particle beam whose travelling direction is deflected by the horizontal deflection electromagnet to a direction which is different from a direction which is parallel to the accelerator median and a second perpendicular electromagnet which deflects the particle beam whose travelling direction is deflected by the first perpendicular deflection to a direction which is parallel to the accelerator median plane, wherein the horizontal deflection electromagnet is provided on a floor which is different from a floor where a particle beam irradiation unit is provided.

6 Claims, 8 Drawing Sheets (52) U.S. Cl.
CPC .............. *A61N 2005/1087* (2013.01); *A61N 2005/1095* (2013.01); *H05H 2007/048* (2013.01)

(56) References Cited

U.S. PATENT DOCUMENTS

| | | |
|---|---|---|
| 2008/0203323 A1 | 8/2008 | Fehrenbacher et al. |
| 2011/0220809 A1* | 9/2011 | Yajima .............. A61N 5/1079 250/396 R |
| 2012/0119106 A1 | 5/2012 | Uno |

FOREIGN PATENT DOCUMENTS

| | | |
|---|---|---|
| JP | 2011-182987 A | 9/2011 |
| JP | 2012-100915 A | 5/2012 |

OTHER PUBLICATIONS

Mitsubishi Electric Corp; News release, "Small type proton beam therapy system is introduced commercially." (Internet:URL:http://www.mitsubishielectric.co.jp/news/2011/1012-b_zoom_02.html).
Taiwanese Office Action issued Oct. 19, 2015, in the corresponding Taiwanese Patent Application No. 103102237 (9 pages).

* cited by examiner

PARTICLE BEAM THERAPY SYSTEM

TECHNICAL FIELD

This invention relates to a particle beam therapy system in which a particle beam is applied, for example, to perform a cancer treatment by irradiating a particle beam.

BACKGROUND ART

According to a particle beam therapy system, high energy charged particles which are accelerated by an accelerator such as a synchrotron are extracted from the accelerator as a particle beam having a beam shape, the particle beam which is extracted is transported to a treatment chamber by a particle beam transport section comprising vacuum ducts, deflection electromagnets, etc. so as to irradiate the particle beam to an affected part of a patient by a particle beam irradiation device.

Regarding a particle beam therapy system, it is necessary to arrange an accelerator, a transport section and a treatment chamber, therefore a relatively large area is needed. In order to reduce installation area, the configuration in which a treatment chamber is arranged at a site whose height is different from that of an accelerator, that is, a treatment chamber is arranged on a floor which is different from that on which an accelerator is arranged is proposed (for example, Patent Document 1, Non-patent document 1).

In Patent Document 1, a particle beam irradiation system has the configuration in which a cyclotron is used as an accelerator, a treatment chamber is arranged directly above an accelerator installation chamber, a particle beam which is emitted from the accelerator is transported to a treatment chamber by a deflection electromagnet for perpendicularly deflecting a particle beam. Further, two treatment chambers are provided, gantry type irradiation devices are arranged radially at each treatment chamber. Switching of particle beam to the two irradiation devices are realized by a mechanism for rotating an electromagnet.

On the other hand, in Non-patent document 1, a particle beam irradiation system has the configuration in which a synchrotron is used as an accelerator, in the same way as that of Patent Document 1, a treatment chamber is arranged directly above an accelerator installation chamber, a particle beam which is extracted from the accelerator is transported to a floor where a treatment chamber is arranged by a deflection electromagnet for perpendicularly deflecting the particle beam and on the floor where a treatment chamber is arranged, the particle beam is further deflected by a deflection electromagnet for horizontally deflecting the particle beam so as to transport to the treatment chamber. In a treatment chamber, a gantry type irradiation device is arranged.

PRIOR ART REFERENCE

Patent Document

[Patent Document 1]
Japanese Patent Application Laid-Open No. 2012-100915
[Non-Patent Document]
Mitsubishi Electric Corp; News release, "Small type proton beam therapy system is introduced commercially."
(Internet:URL:http://www.mitsubishielectric.co.jp/news/2011/1012-b_zoom_02.html)

DISCLOSURE OF THE INVENTION

Problems to be Solved by the Invention

In a particle beam therapy system which is disclosed in Patent Document 1, gantry type irradiation devices are arranged radially, therefore, in some cases, it is difficult to arrange a particle beam therapy system in a site whose width is limited. In general, a particle beam has a momentum dispersion function at an exit of a circular accelerator, and in order to make the dispersion function zero at a desired position, it is necessary to design a beam line considering the above-mentioned. In a position where a momentum dispersion function is not zero, by spread of the momentum of beam, a beam region is increased and correlation between a beam distribution and a momentum is generated. Further, in a case where the center momentum of a beam changes depending on time, a beam position changes depending on time. At an isocenter where a particle beam is irradiated to an affected part, in order to make the variation in a position of a beam minimum while a beam region is reduced and a distribution is made to be uniform, it is necessary to deflect a particle beam in a plane which is parallel to a median plane of a circular accelerator so as to make a momentum dispersion function in a direction which is parallel to an accelerator median plane zero. However, according to the configuration of a particle beam therapy system disclosed in Patent Document 1, a particle beam is not deflected in a plane which is parallel to an accelerator median plane. Therefore, a momentum dispersion function in a direction which is parallel to an accelerator median plane can not make zero, a beam size is increased, a deviation of a beam distribution which has the correlation with a momentum is generated, and the variation in positions of a beam might become large. Consequently, it might become difficult to form a desired dose distribution in an irradiation subject.

On the other hand, in a particle beam therapy system which is disclosed in Non-patent document 1, a momentum dispersion function in a direction which is parallel to an accelerator median plane can be made zero. Further, the configuration of the particle beam therapy system is suitable for a case where the particle beam therapy is provided at a site which is similar to a regular square shape. However, it is necessary to arrange a deflection electromagnet on a floor where a treatment chamber is arranged, therefore, space utilization of a floor where a treatment chamber is arranged is inefficient.

In order to solve the above-mentioned problems of conventional particle beam therapy system, the present invention aims to provide a particle beam therapy system having efficient space utilization of a floor where a treatment chamber is provided while a problem, that is, a momentum dispersion function of a particle beam which is extracted from a circular accelerator exists is solved.

Means for Solving the Problems

According to the present invention, a particle beam therapy system comprises a circular accelerator which accelerates a particle beam, a particle beam transport section which transports a particle beam which is emitted from the circular accelerator, and a particle beam irradiation unit which irradiates the particle beam which is transported by the particle beam transport section and is provided on a floor which is different from that on which the circular accelerator is provided, wherein the particle beam transport section comprises a horizontal deflection electromagnet which deflects a particle beam to a direction which is parallel to an accelerator median plane, a first perpendicular deflection electromagnet which deflects the particle beam whose travelling direction is deflected by the horizontal deflection electromagnet to a direction which is different from a direction which is parallel to the accelerator median plane and a second perpendicular deflection electromagnet which deflects the particle beam whose direction is deflected by the first perpendicular deflection electromagnet to a direction which is parallel to the accelerator median plane, and the horizontal deflection electromagnet is provided on a floor which is different from a floor on which the particle beam irradiation unit is provided.

Advantage of the Invention

According to the present invention, a problem, that is, a momentum dispersion function of a particle beam which is extracted from a circular accelerator exists is solved and a particle beam therapy system having an efficient space utilization of a floor where a treatment chamber is arranged can be provided.

EMBODIMENTS FOR CARRYING OUT THE INVENTION

Embodiment 1

Figure 1:
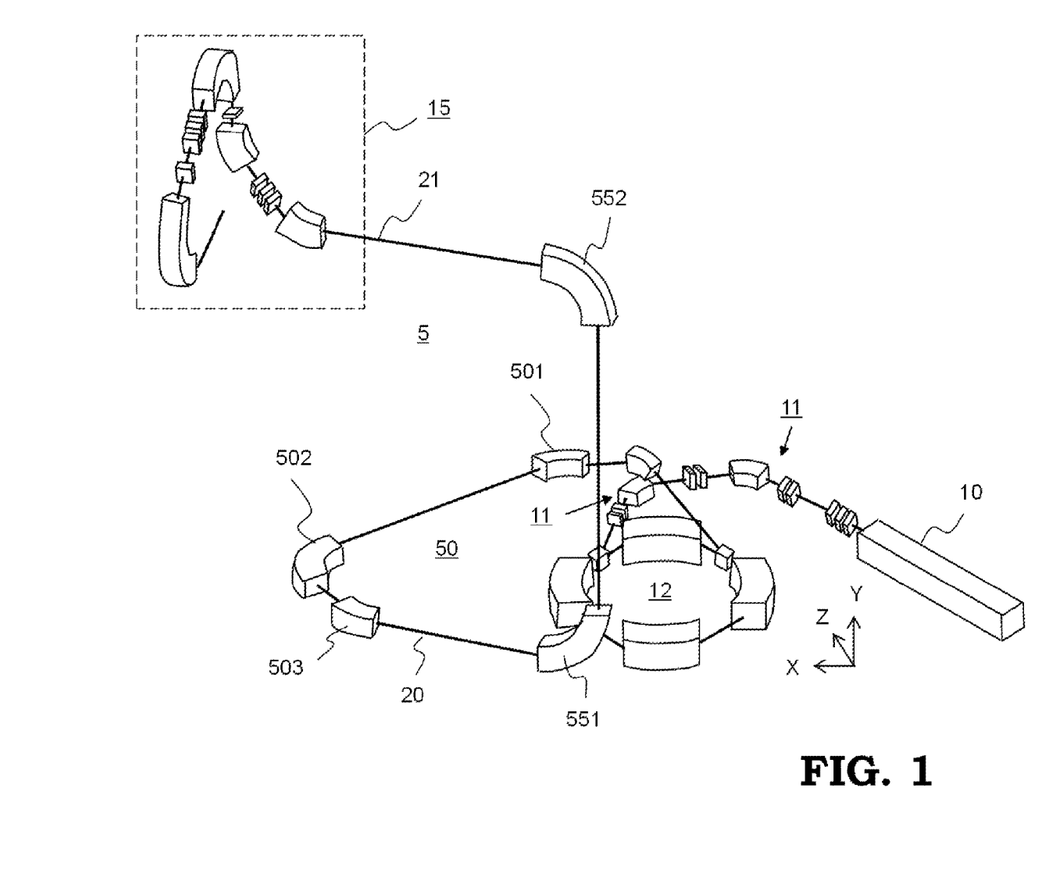
FIG. 1 is a perspective view showing the layout of main equipment of a particle beam therapy system according to EMBODIMENT 1 of the present invention.

FIG. 1 is a perspective view showing the schematic configuration of a particle beam therapy system according to EMBODIMENT 1 of the present invention. FIG. 1 shows only the arrangement of main equipment of a particle beam therapy system. A particle beam therapy system comprises an injector 10, a low energy particle beam transport section 11, a circular accelerator 12 such as a synchrotron, a high energy particle beam transport section 5, and a subsystem such as a rotating gantry 15.

Next, basic operation and configuration of a particle beam therapy system according to EMBODIMENT 1 will be described. A particle beam which is an aggregation of ion (for example, a hydrogen ion, a carbon ion) which is generated at an ion source of the injector 10 is preliminarily accelerated by a pre-linear accelerator of the injector 10 so as to be accelerated to be specified kinetic energy. The particle beam which is preliminarily accelerated is extracted from the injector 10, passed through a low energy particle beam transport section 11 in which various kinds of electromagnets are arranged and is guided to the circular accelerator 12. In FIG. 1, a synchrotron is shown as a circular accelerator. In the circular accelerator 12, various kinds of electromagnets including deflection electromagnets, electromagnets for correcting an orbit and quadrupole electromagnets for converging or diverging are arranged so as for a particle beam to circulate around an orbit in the circular accelerator 12, and the particle beam receives repeatedly an accelerating electric field which is formed by a high frequency acceleration cavity. A particle beam is repeatedly accelerated by the accelerating electric field of the high frequency acceleration cavity and its kinetic energy is increased together with acceleration. As kinetic energy increases, a magnetic field strength which is necessary to deflect a particle beam changes. Consequently, regarding equipment including various kinds of electromagnets constituting the circular accelerator 12, its operation parameter changes according to time. At the timing when kinetic energy of a particle beam in the circular accelerator 12 reaches specified kinetic energy and the particle beam can be extracted, the particle beam is transported to the high energy particle beam transport section 5 (simply, refers as a particle beam transport section 5) by a beam extracting device.

A plane where a particle beam circulates around an orbit in the circular accelerator 12 is referred to as an accelerator median plane. In the particle beam transport section 5, a travelling direction of a particle beam is changed by a deflection electromagnet, and the particle beam is transported to a particle beam irradiation unit 15 such as a rotating gantry for irradiating a particle beam to an affected part of a patient. Hereinafter, the particle beam irradiation unit 15 will be described as a rotating gantry 15. In the particle beam transport section 5, horizontal deflection electromagnets 501, 502 and 503, a first perpendicular deflection electromagnet 551 for deflecting a particle beam to a direction except for a direction which is parallel to the accelerator median plane and a second perpendicular deflection electromagnet 552 for returning the particle beam to a direction which is parallel to the accelerator median plane are provided. It is necessary for a part where a particle beam passes through to be vacuum not for a particle beam to be scattered, and the particle beam passes through a vacuum duct which is included in the particle beam transport section 5. In the particle beam transport section 5, as needed, other items including electromagnets for converging or diverging the particle beam are arranged.

As above mentioned, in the particle beam transport section 5, the first perpendicular deflection electromagnet 551 and the second perpendicular deflection electromagnet 552 are arranged, a particle beam is transported to a height which is different from that of the accelerator median plane of the circular accelerator 12, and a particle beam irradiation unit is provided on a floor which is different from a floor where the circular accelerator 12 is provided. On the other hand, the horizontal deflection electromagnets 501, 502 and 503 are provided on a floor where the circular accelerator 12 is provided.

In this specification, in a case where a particle beam is travelling in a plane which is parallel to the accelerator median plane, when a travelling direction of a particle beam is defined as a Z-direction, a direction which is perpendicular to the Z-direction and in the accelerator median plane or in a plane which is parallel to the accelerator median plane is defined as an X-direction, and a direction which is perpendicular to the Z-direction and the X-direction is defined as a Y-direction, description will be made. Consequently, an X-Z plane is parallel to the accelerator median plane and is horizontal plane, and a Y-direction is perpendicular to the plane, that is, a vertical direction. A particle beam which is extracted from a circular accelerator such as a synchrotron accelerator has a momentum dispersion function in a direction of a plane which is perpendicular to a travelling direction of the particle beam at an exit of a circular accelerator. In order to make a momentum dispersion function zero at an isocenter, it is necessary to design the particle beam therapy system considering a momentum dispersion function at an exit of a circular accelerator. When a particle beam which is extracted has a momentum dispersion function at an isocenter, a beam position on the isocenter is varied, therefore, it is difficult to form a desired dose distribution in an affected part of a patient which is an irradiation objective. By deflecting a particle beam to the X-direction, that is, to a horizontal direction, a momentum dispersion function in the X-direction at the isocenter can be made zero. Consequently, in order to adjust a momentum dispersion function in the X-direction, it is necessary to deflect a particle beam in a plane which is parallel to the accelerator median plane. That is, it is necessary to provide the horizontal deflection electromagnets 501, 502 and 503 in a plane which is parallel to the accelerator median plane.

Figure 2:
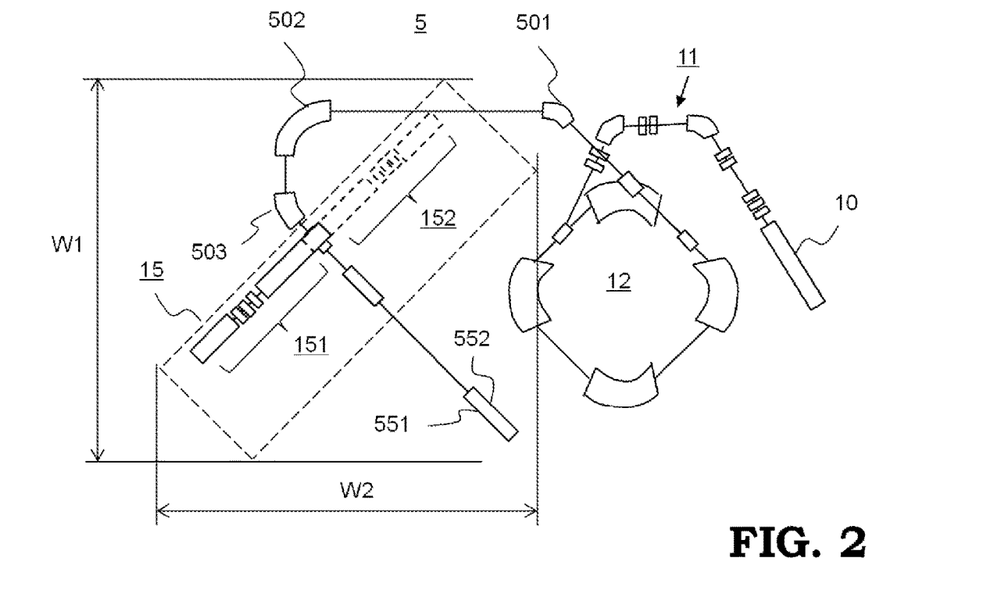
FIG. 2 is a top view showing the layout of main equipment of a particle beam therapy system according to EMBODIMENT 1 of the present invention.

Regarding a particle beam therapy system according to EMBODIMENT 1 of the present invention, a group of horizontal deflection electromagnets 50 comprising the horizontal deflection electromagnets 501, 502 and 503 are provided on a floor where the circular accelerator 12 is provided, that is, a floor which is different from a floor where the rotating gantry 15 which is a particle beam irradiation unit is provided. FIG. 2 is a top view showing the whole of a particle beam therapy system according to EMBODIMENT 1 of the present invention. As the rotating gantry 15 rotates, therefore, a large space is needed. When a constituent member 151 of the rotating gantry 15 shown in FIG. 2 rotates 180 degrees, the rotating gantry is arranged at a position of a constituent member 152 which is designated by a broken line. Consequently, as the rotating gantry, when a mechanism for rotating a constituent member is included, at least a space of a rectangle which is designated by a broken line is needed. As shown in FIG. 2, a space of a rotating gantry chamber at which the rotating gantry 15 is provided in the top view is obtained by integrating a width W1 and a width W2. For example, in a case where a rotating gantry is arranged in which a rotating axis is an arbitrary angle, (in FIG. 2, 45 degrees), a width W1 and a width W2 which determine a size of the rotating gantry chamber is substantially determined by a width which is occupied by the rotating gantry 15.

On the other hand, according to a particle beam therapy system disclosed in Non-Patent Document 1, a horizontal deflection electromagnet is provided on a floor where a rotating gantry is provided. Consequently, there is a merit such that it is easy to arrange a rotating gantry right above a circular accelerator. However, for convenience of flexibility of arrangement or adjustment, in general, a plurality of horizontal deflection electromagnets are needed. Consequently, it is necessary to provide horizontal deflection electromagnets as a group of horizontal deflection electromagnets, therefore, a space of the particle beam transport section 5 for arranging the group of horizontal deflection electromagnets is needed. Therefore, according to the particle beam therapy system disclosed in Non-Patent Document 1, regarding a size of the rotating gantry chamber, a space which is obtained by adding at least a space of a part constituting a group of horizontal deflection electromagnets to a space which is occupied by the gantry space is needed.

Figure 3:
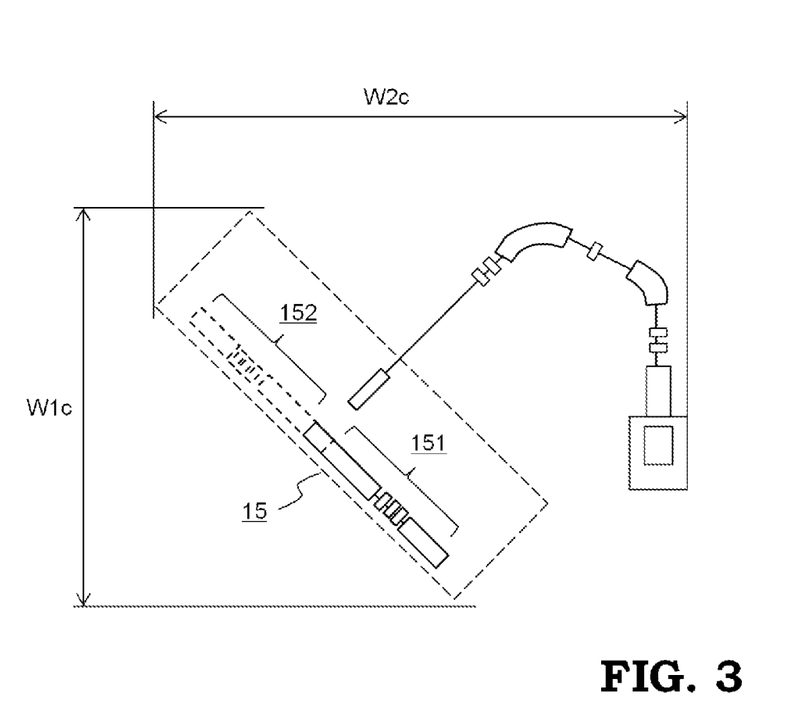
FIG. 3 is a top view showing the layout of main equipment on a floor where a rotating gantry of a particle beam therapy system which is disclosed in Non-patent document 1 is arranged.

Regarding the particle beam therapy system disclosed in Non-Patent Document 1, in order to compare with a particle beam therapy system according to EMBODIMENT 1 of the present invention, a top view of a floor where a rotating gantry is provided is shown in FIG. 3. As shown in FIG. 3, in a region in which a size of a particle beam transport section constituting of a group of horizontal deflection electromagnets is added to a region which is occupied by the rotating gantry 15, a width of a rotating gantry chamber W1c and a width of a rotating gantry chamber W2c are determined, therefore, a rotating gantry chamber which is larger than that of EMBODIMENT 1 of the present invention is needed. Therefore, when a limited total floor area is given, in comparison with a particle beam therapy system disclosed in Non-Patent Document 1, regarding a particle beam therapy system of the present invention, a total floor area where a rotating gantry, which is a particle beam irradiation unit, is provided can be allocated to other medical chambers except for the rotating gantry chamber, as a result, a total floor area can be effectively utilized.

Further, regarding a particle beam therapy system according to EMBODIMENT 1 of the present invention, in a case where the rotating gantry 15 is projected on a floor where the group of horizontal deflection electromagnets 50 are provided, the rotating gantry 15 is arranged at a position which is overlapped with the particle beam transport section 5 including the group of horizontal deflection electromagnets 50. Consequently, the particle beam therapy system can be provided at a site whose width of one direction is smaller. According to EMBODIMENT 1 of the present invention, it is configured such that a travelling direction of a particle beam 20 which is inputted to the first perpendicular deflection electromagnet 551 which is provided at the back of the group of horizontal deflection electromagnets 50 comprising the horizontal deflection electromagnet 501, 502 and 503 shown in FIG. 1 is opposite to a travelling direction of a particle beam 21 which is outputted from the second perpendicular deflection electromagnet 552 on a floor where the rotating gantry 15 is arranged. Consequently, the projection of a particle beam irradiation unit to a floor where the horizontal deflection electromagnets are provided can be performed so as to overlap with the particle beam transport section on the floor where the horizontal deflection electromagnets are provided. As above mentioned, in a particle beam therapy system according to EMBODIMENT 1 of the present invention, the layout can be realized so as to make a width of projection W1 including the rotating gantry 15 and whole of the particle beam transport section 5 minimum. As a result, a particle beam therapy system can be provided at a site whose width of one direction is smaller.

Embodiment 2

Figure 4:
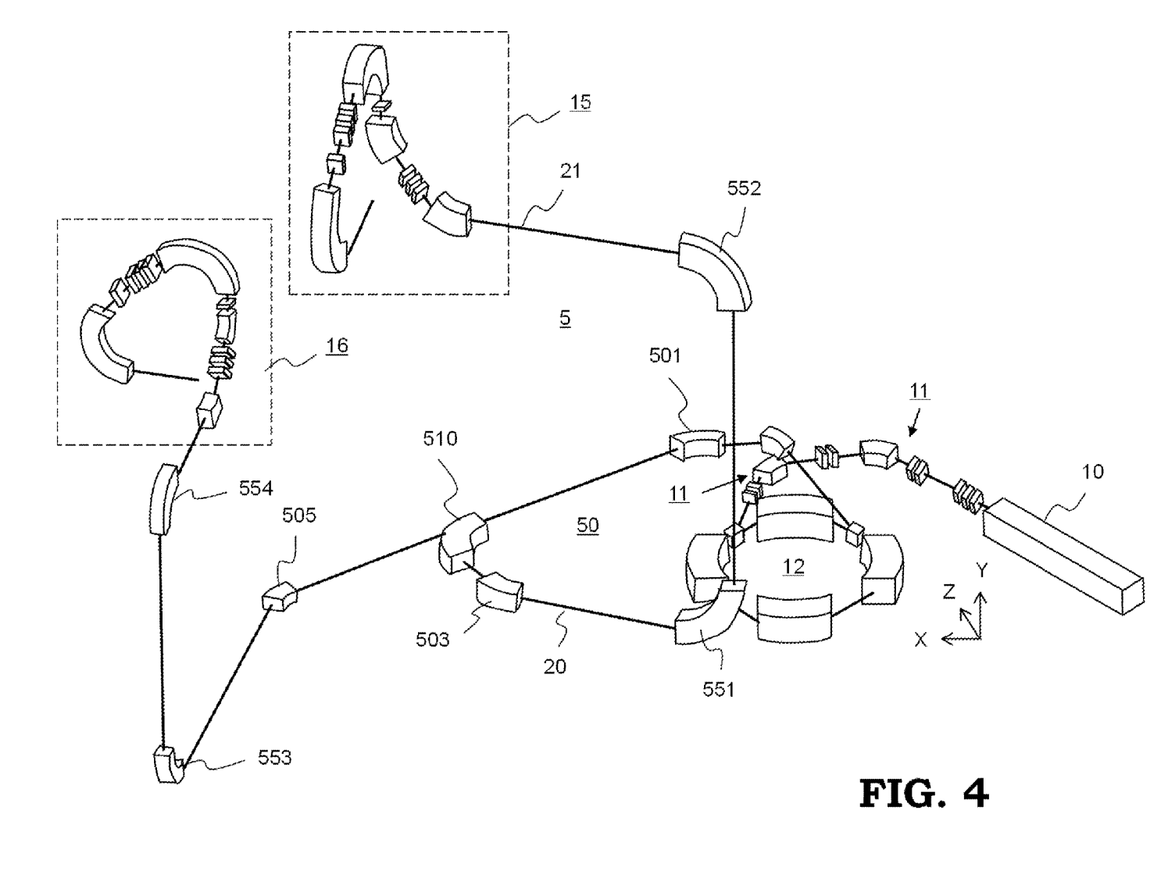
FIG. 4 is a perspective view showing the layout of main equipment of a particle beam therapy system according to EMBODIMENT 2 of the present invention.

FIG. 4 is a perspective view showing the layout of main equipment of a particle beam therapy system according to EMBODIMENT 2 of the present invention. EMBODIMENT 2 describes a particle beam therapy system comprising two rotating gantries, that is, a rotating gantry 15 and a rotating gantry 16. Also in EMBODIMENT 2, a group of horizontal deflection electromagnets 50 comprising horizontal deflection electromagnets 501, 503, 505 and 510 are provided on a floor which is different from a floor where the rotating gantries are provided. Here, the horizontal deflection electromagnet 510 has a branch function for switching so as to transport a particle beam to either of the rotating gantry 15 or the rotating gantry 16.

Figure 5:
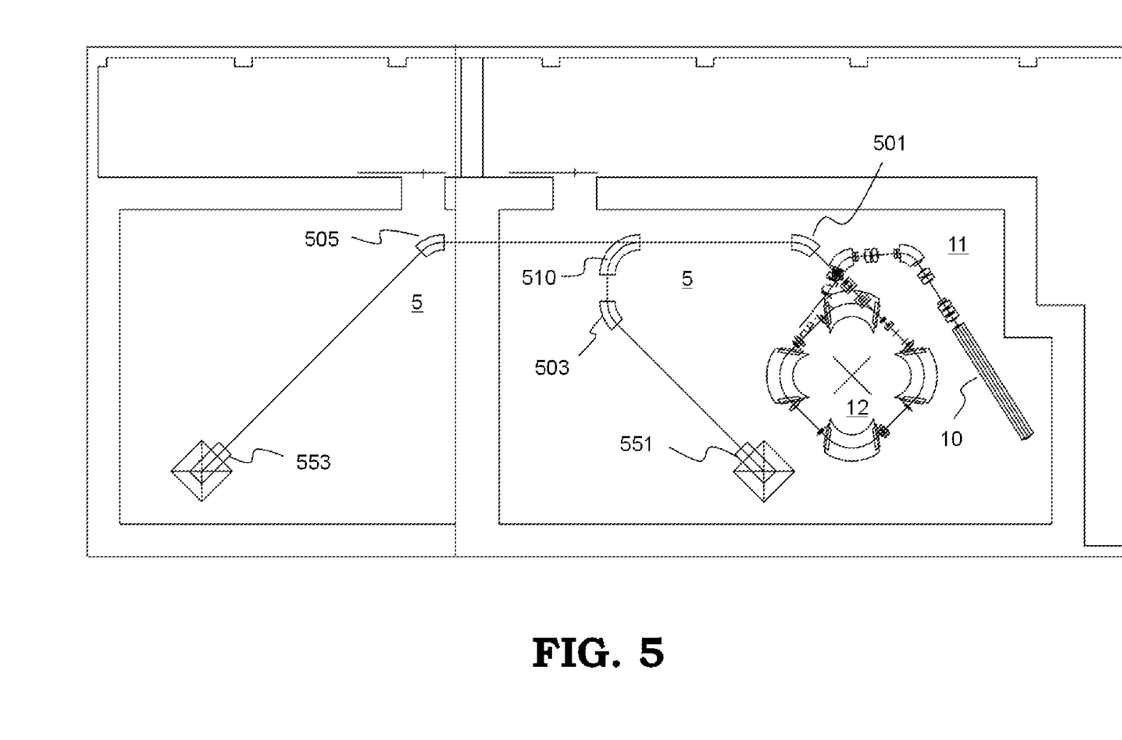
FIG. 5 is a top view showing the layout of main equipment on a floor where a circular accelerator and a group of horizontal deflection electromagnets of a particle beam therapy system according to EMBODIMENT 2 of the present invention are arranged.
Figure 6:
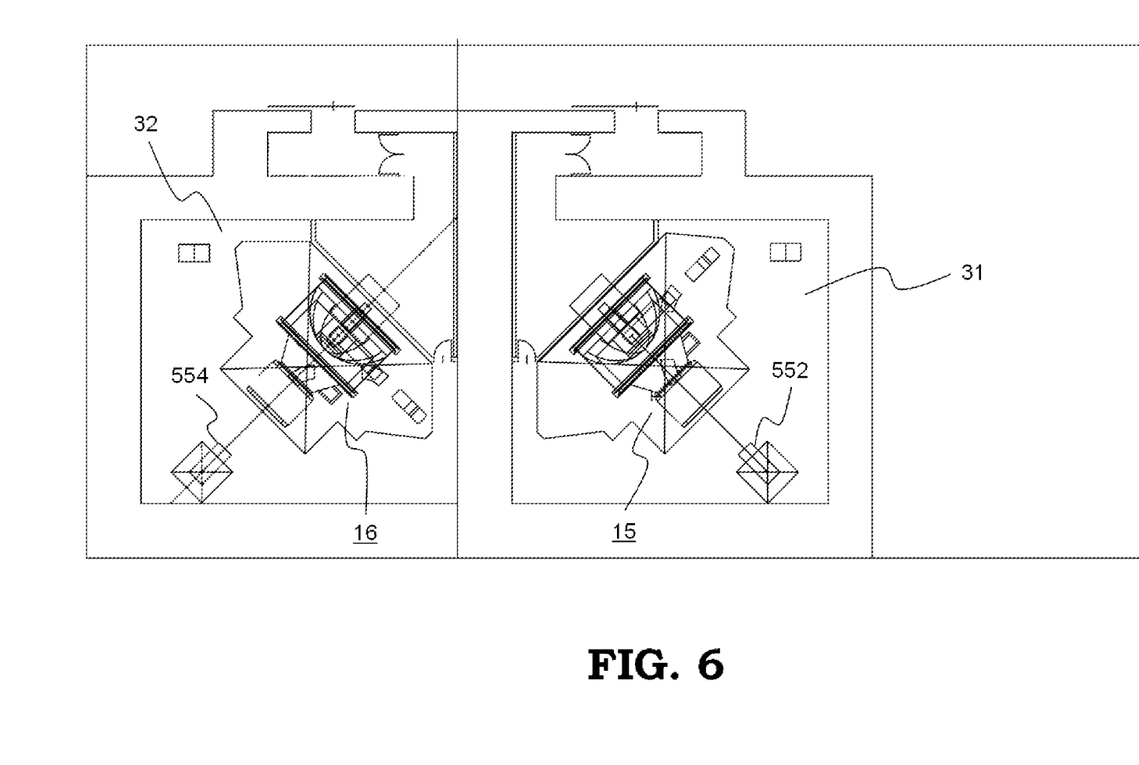
FIG. 6 is a top view showing the layout of main equipment on a floor where a rotating gantry which is a particle beam irradiation unit of a particle beam therapy system according to EMBODIMENT 2 of the present invention is provided.

FIG. 5 is a top view showing a floor where a circular accelerator 12 and the group of horizontal deflection electromagnets 50 are provided, and FIG. 6 is a top view showing a floor where the rotating gantry 15 and the rotating gantry 16 are provided. The rotating gantry 15 is provided in a treatment chamber 31 and the rotating gantry 16 is provided in a treatment chamber 32. As shown in FIG. 5, a particle beam to be transported to the rotating gantry 15 is transported upward by a first perpendicular deflection electromagnet 551 which is arranged right under the treatment chamber 31 and is guided to the rotating gantry 15 by a second perpendicular deflection electromagnet 552 in the treatment chamber 31 shown in FIG. 6. On the other hand, a particle beam to be transported to the rotating gantry 16 is transported upward by a first perpendicular deflection electromagnet 553 which is arranged right under the treatment chamber 32 and is guided to the rotating gantry 16 by a second perpendicular deflection electromagnet 554 in the treatment chamber 32.

Also in a particle beam therapy system according to EMBODIMENT 2 of the present invention, the group of horizontal deflection electromagnets 50 is provided on a floor which is different from that where the rotating gantries are provided. Consequently, in the same way as that of EMBODIMENT 1, a size of a part of the rotating gantry chambers can be minimum. Further in a case where the rotating gantry 15 and the rotating gantry 16 are projected to a floor where the group of horizontal deflection electromagnets 50 are provided, even at a position which overlaps with a position of a particle beam transport section 5 including the group of horizontal deflection electromagnets 50, the rotating gantry 15 and the rotating gantry 16 can be arranged. Consequently, a width of projection of whole of system as shown in FIG. 4 can be same as a width which is occupied by the rotating gantry 15 and the rotating gantry 16, and as shown in FIG. 5 and FIG. 6, the whole of a particle beam therapy system can be provided at a long and narrow site.

Embodiment 3

Figure 7:
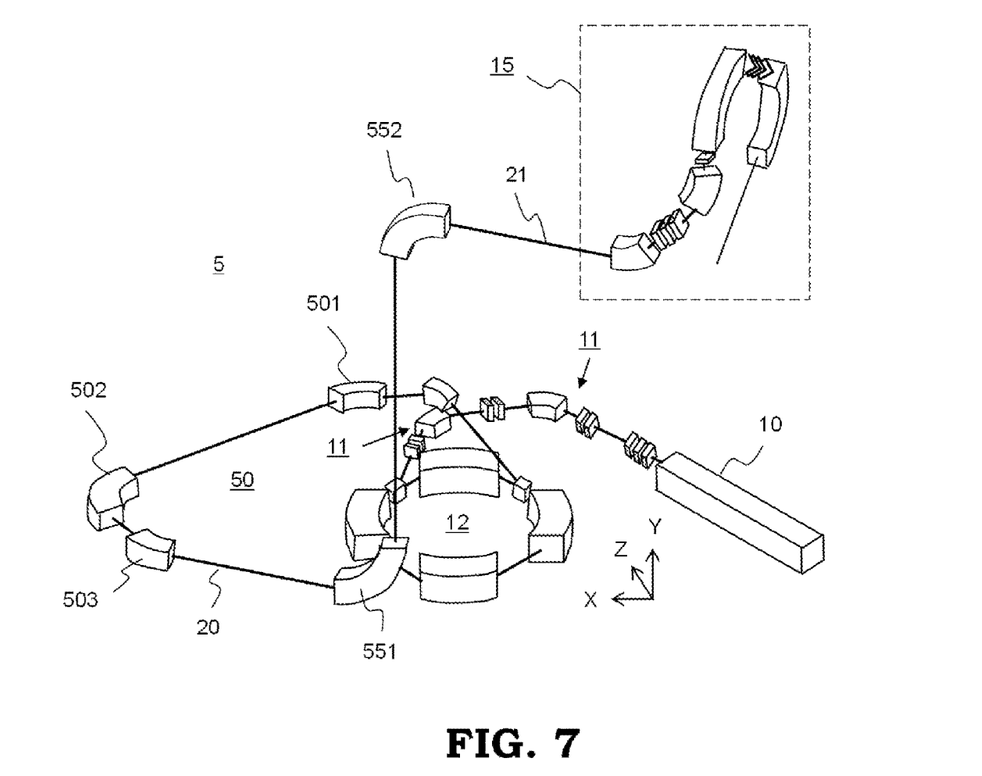
FIG. 7 is a perspective view showing the layout of main equipment of a particle beam therapy system according to EMBODIMENT 3 of the present invention.
Figure 8:
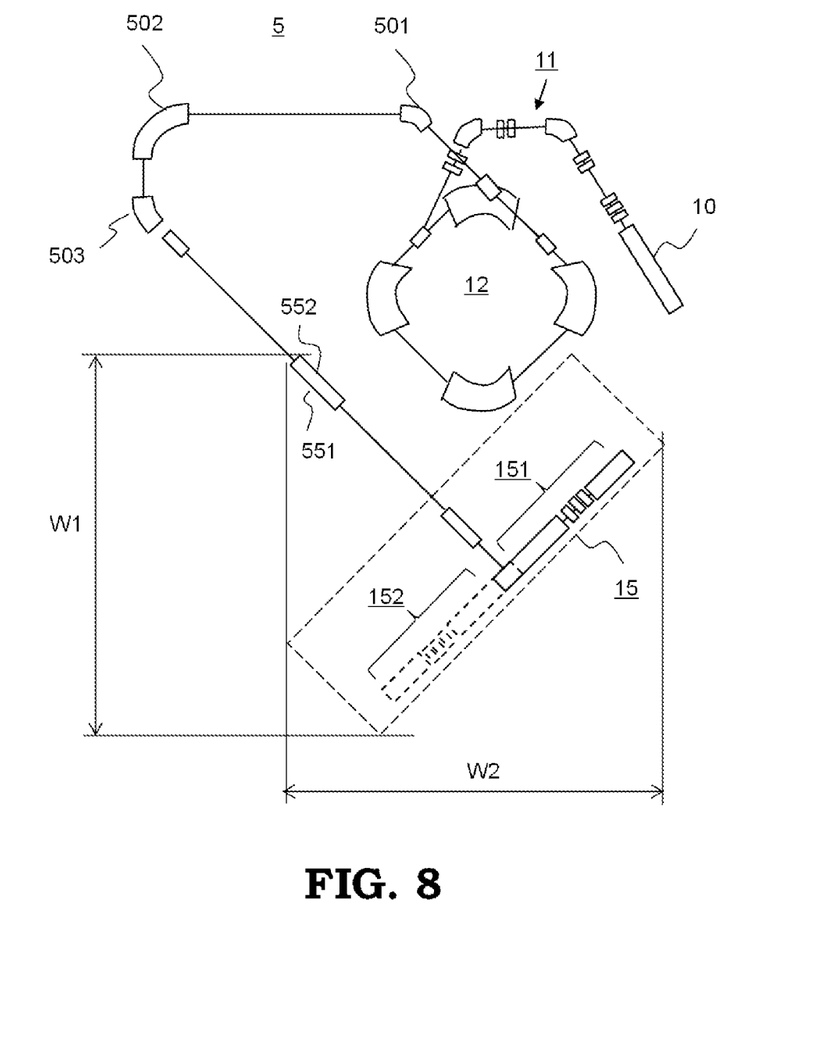
FIG. 8 is a top view showing the layout of main equipment of a particle beam therapy system according to EMBODIMENT 3 of the present invention.

FIG. 7 is a perspective view showing the layout of main equipment of a particle beam therapy system according to EMBODIMENT 3 of the present invention. In EMBODIMENT 1 and EMBODIMENT 2, it is configured such that a direction of a particle beam 20 which travels to a first perpendicular deflection electromagnet 551 which is provided at the back of a group of horizontal deflection electromagnets 50 is opposite to a direction of a particle beam 21 which travels from a second perpendicular deflection electromagnet 552 on a floor where a rotating gantry 15 is arranged to the rotating gantry 15. However, it is not necessary to have the above-mentioned configuration, as shown in FIG. 7, it may be configured such that a direction of the particle beam 21 which travels from the second perpendicular deflection electromagnet 552 on a floor where the rotating gantry 15 is arranged to the rotating gantry 15 is opposite to a direction in EMBODIMENT 1 and EMBODIMENT 2. Further, a direction of the particle beam 21 from the second perpendicular deflection electromagnet 552 to the rotating gantry 15 is not limited to an opposite direction with respect to a direction of the particle beam 20 which travels to the first perpendicular deflection electromagnet 551, and may be an arbitrary direction. FIG. 8 is a top view of FIG. 7. As shown in FIG. 8, in the same way as that of EMBODIMENT 1 of the present invention, a space which is occupied by a rotating gantry is W1×W2, total floor area where a particle beam irradiation unit is provided can be allocated to other medical chamber except for a rotating gantry chamber, as a result, a total floor area can be effectively utilized.

5: particle beam transport section
12: circular accelerator
15, 16: rotating gantry (particle beam irradiation unit)
50: a group of horizontal deflection electromagnets
501, 502, 503, 505, 510: horizontal deflection electromagnet
551, 553: a first perpendicular deflection electromagnet
552, 554: a second perpendicular deflection electromagnet

The invention claimed is:

1. A particle beam therapy system comprising:
a circular accelerator which accelerates a particle beam,
a particle beam transport section which transports the particle beam which is extracted from the circular accelerator and
a particle beam irradiation unit which irradiates the particle beam which is transported by the particle beam transport section which is provided on a floor which is different from a floor where the circular accelerator is provided,
wherein the particle beam transport section comprises a horizontal deflection electromagnet which deflects the particle beam, which is travelling in a plane which is parallel to an accelerator median plane of the circular accelerator, in the plane which is parallel to the accelerator median plane of the circular accelerator,
a first perpendicular deflection electromagnet which deflects the particle beam whose travelling direction is deflected by the horizontal deflection electromagnet to a direction which is different from a direction which is parallel to the accelerator median plane and
a second perpendicular deflection electromagnet which deflects the particle beam whose direction is deflected by the first perpendicular deflection electromagnet to a direction which is parallel to the accelerator median plane,
wherein the horizontal deflection electromagnet is provided on a floor which is different from a floor where the particle beam irradiation unit is provided.

2. The particle beam therapy system as claimed in claim 1,
wherein a particle beam irradiation unit is arranged at a position which overlaps with the particle beam transport section on a floor where the horizontal deflection electromagnet is provided.

3. The particle beam therapy system as claimed in claim 1,
wherein the particle beam irradiation unit has a rotating gantry.

4. The particle beam therapy system as claimed in claim 1,
wherein the horizontal deflection electromagnet comprises a plurality of deflection electromagnets and all of the horizontal deflection electromagnets are provided on a floor which is different from a floor where the particle beam irradiation unit is provided.

5. The particle beam therapy system as claimed in claim 4, wherein a plurality of the particle beam irradiation units are provided and at least one of the horizontal deflection electromagnets constituting the plurality of deflection electromagnets has a function to branch a particle beam to two directions.

6. The particle beam therapy system as claimed in claim 1, wherein a travelling direction of the particle beam which is inputted to the first perpendicular deflection electromagnet is opposite to a travelling direction of the particle beam which is outputted from the second perpendicular deflection electromagnet.

* * * * *